US00PP34501P3

(12) United States Plant Patent
Kobayashi et al.

(10) Patent No.: US PP34,501 P3
(45) Date of Patent: Aug. 16, 2022

(54) ***IPOMOEA BATATAS* PLANT NAMED 'CHURAKANASA'**

(50) Latin Name: *Ipomoea batatas*
Varietal Denomination: Churakanasa

(71) Applicant: National Agriculture and Food Research Organization, Tsukuba (JP)

(72) Inventors: Akira Kobayashi, Ibaraki (JP); Yumi Kai, Ibaraki (JP); Takeo Sakaigaichi, Ibaraki (JP); Keisuke Suematsu, Ibaraki (JP); Katsuya Ichinose, Ibaraki (JP); Yoshihiro Okada, Ibaraki (JP)

(73) Assignee: NATIONAL AGRICULTURE AND FOOD RESEARCH ORGANIZATION, Ibaraki (JP)

( * ) Notice: Subject to any disclaimer, the term of this patent is extended or adjusted under 35 U.S.C. 154(b) by 0 days.

(21) Appl. No.: 17/300,123

(22) Filed: Mar. 15, 2021

(65) Prior Publication Data

US 2021/0321549 P1 Oct. 14, 2021

(30) Foreign Application Priority Data

Mar. 17, 2020 (JP) ..... PBR 34567

(51) Int. Cl.
*A01H 6/00* (2018.01)
*A01H 5/12* (2018.01)

(52) U.S. Cl.
USPC ..... Plt./258
CPC ..... *A01H 6/00* (2018.05)

(58) Field of Classification Search
USPC ..... Plt./258
See application file for complete search history.

(56) References Cited

U.S. PATENT DOCUMENTS

| | | | | |
|---|---|---|---|---|
| PP17,976 P2 * | 9/2007 | Sizemore | A01H 5/06 Plt./258 |
| PP21,743 P2 * | 3/2011 | Yencho | A01H 5/06 Plt./258 |
| PP21,744 P2 * | 3/2011 | Yencho | A01H 5/06 Plt./258 |
| PP27,940 P2 * | 4/2017 | Jandrew | A01H 5/12 Plt./263.1 |

* cited by examiner

*Primary Examiner* — Susan McCormick Ewoldt
*Assistant Examiner* — Karen M Redden
(74) *Attorney, Agent, or Firm* — McCarter & English, LLP; David G. Conlin

(57) ABSTRACT

'Churakanasa' is a new variety of sweet potato bred by hybridizing variety 'Purple Sweet Lord' and '90IDN-47' in 2009. The plant may be used, e.g., for cultivation of root tubers for consumption.

9 Drawing Sheets

Plant name and variety denomination:

Latin name of the genus and species of the plant claimed: *Ipomoea batatas* (L.) Lam. The claimed plant is a hybridization of different varieties of *Ipomoea batatas*.

Common name of the claimed plant's species: sweet potato.

Variety denomination: 'Churakanasa'.

CROSS REFERENCE TO RELATED APPLICATION

The present application claims priority to Japanese Plant Variety Registration No. 34567 filed Mar. 17, 2020, the entire contents of which is incorporated herein for all purposes by this reference.

BACKGROUND

*Ipomoea batatas*, commonly called sweet potato or sweet potato vine, is a dicotyledonous plant that belongs to the bindweed or morning glory family, Convolvulaceae. It is an herbaceous perennial that is cultivated for its edible root tubers. *Ipomoea batatas* is native to tropical regions of the Americas.

Because sweet potatoes are very strong against climate disasters, such as typhoons and droughts, sweet potatoes are significant crops in Okinawa. Purple colored sweet potato produced in Okinawa is specifically called 'Beniimo' which means red sweet potato. Processed paste confectionaries which utilize the color tone of purple colored sweet potato are popular as souvenirs.

BRIEF SUMMARY

'Churakanasa' is a new variety of *Ipomoea batatas* bred by hybridization of variety 'Purple Sweet Lord' (not patented) as the female parent and '90IDN-47' (not patented; genetic resource of Indonesia) as the male parent. The plant may be used, e.g., for cultivation of root tubers for consumption.

'Churakanasa' is a purple-colored sweet potato lineage. The weight of the yield of good quality storage roots of 'Churakanasa' is comparable to that of the high yield variety 'Churakoibeni' (not patented) in conventional spring planting. In autumn planting cultivation, the yield (total weight) of the good quality storage roots of 'Churakanasa' is greater than that of 'Churakoibeni', thus the introduction of autumn planting cultivation of 'Churakanasa' is possible. The color value representing the anthocyanin content of 'Churakanasa' is moderately higher than that of 'Churakoibeni'. The color tone of the flesh paste is moderately more bluish than that of 'Churakoibeni', but the processability of 'Churakanasa' into paste and red sweet potato tart was evaluated to be the same level as that of 'Churakoibeni'.

DETAILED BOTANICAL DESCRIPTION OF THE PLANT

Variety: 'Churakanasa'

Figure 1:
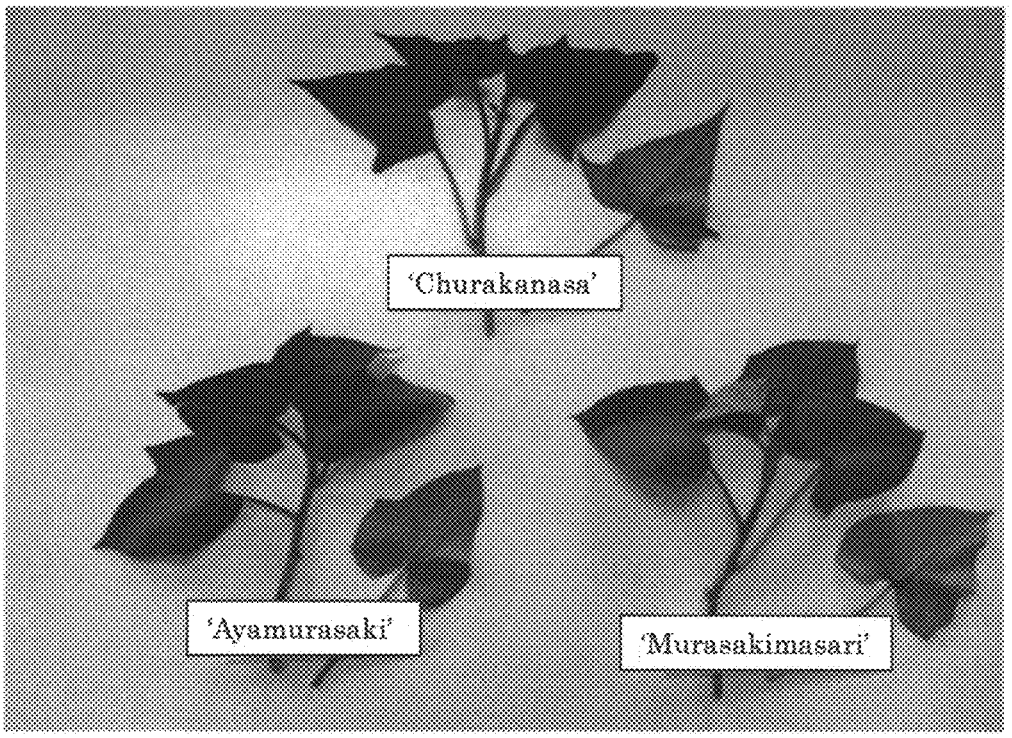
FIG. 1 is a photograph of the above-ground or aerial portions of 'Churakanasa' (top) compared to similar varieties 'Ayamurasaki' (bottom left) and 'Murasakimasari' (bottom right) 112 days after planting.
Figure 2:
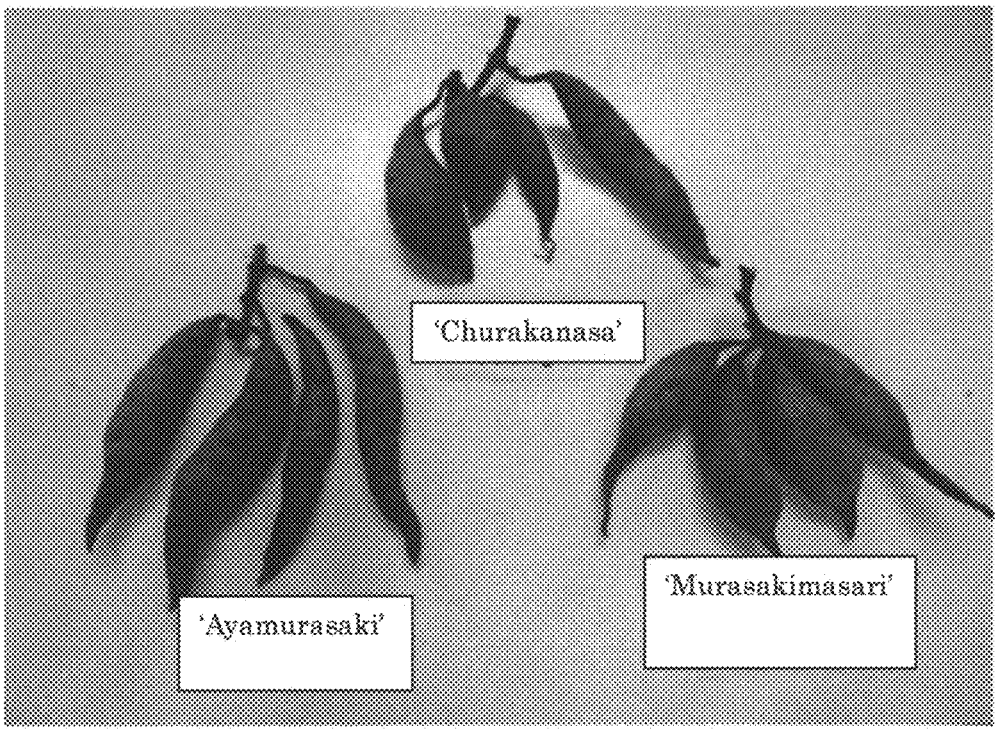
FIG. 2 is a photograph of the below-ground or subterranean portions of 'Churakanasa' (top) compared to similar varieties 'Ayamurasaki' (bottom left) and 'Murasakimasari' (bottom right) 154 days after planting.
Figure 3:
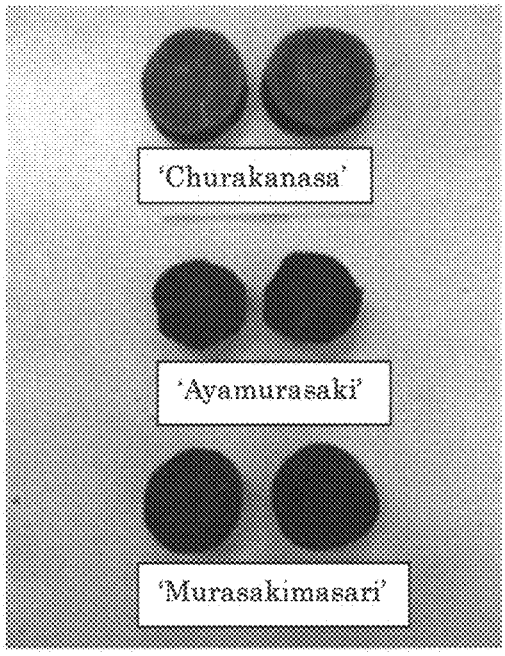
FIG. 3 is a photograph of a cross-sectional view of the storage roots or subterranean portions of 'Churakanasa' (top) compared to similar varieties 'Ayamurasaki' (middle) and 'Murasakimasari' (bottom) 154 days after planting showing the colors of the storage roots.
Figure 4:
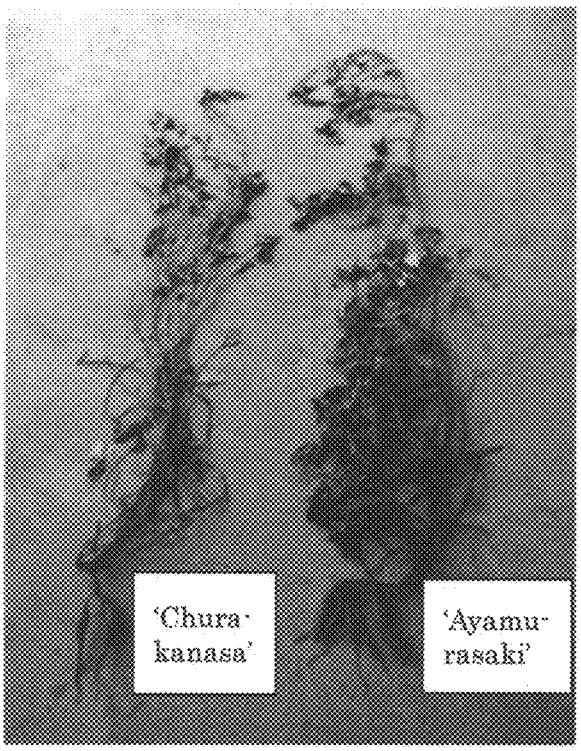
FIG. 4 is a photograph of the whole plant body of 'Churakanasa' (left) compared to the similar variety 'Ayamurasaki' (right) 122 days after planting.
Figure 5:
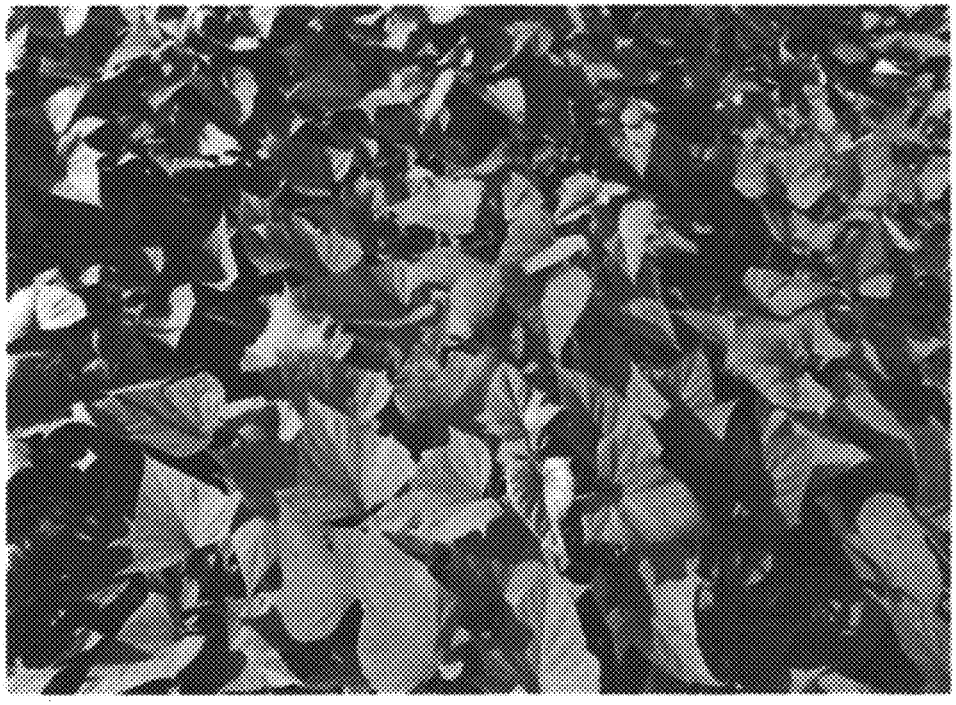
FIG. 5 is a photograph of the cultivation zone of 'Churakanasa' 63 days after planting.
Figure 6:
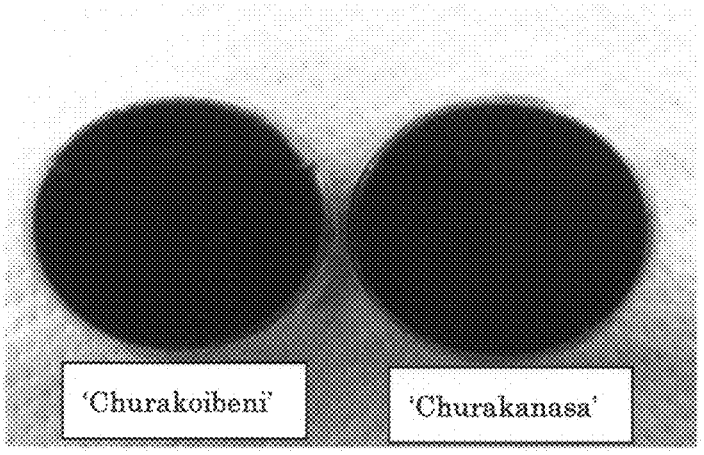
FIG. 6 is a photograph of the paste produced from 'Churakanasa' (right) and similar variety 'Churakoibeni' (left) 5 months and 2 weeks after planting.
Figure 7:
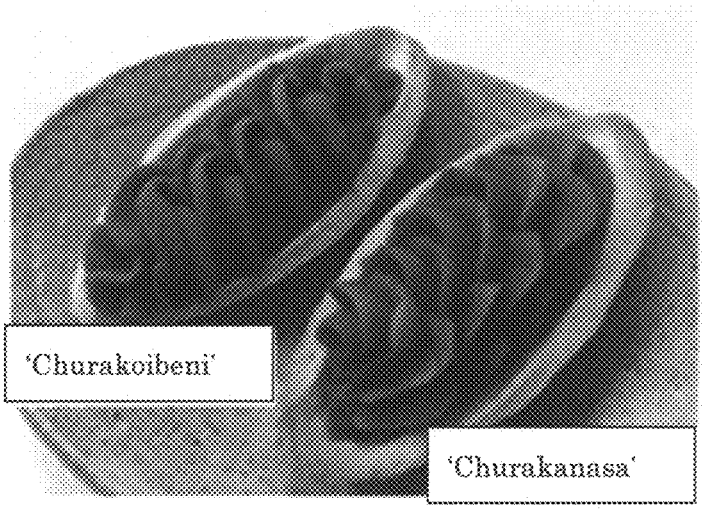
FIG. 7 is a photograph of Beniimo (red sweet potato) tarts prepared using paste from 'Churakanasa' (right) and similar variety 'Churakoibeni' (left) 5 months and 2 weeks after planting.
Figure 8:
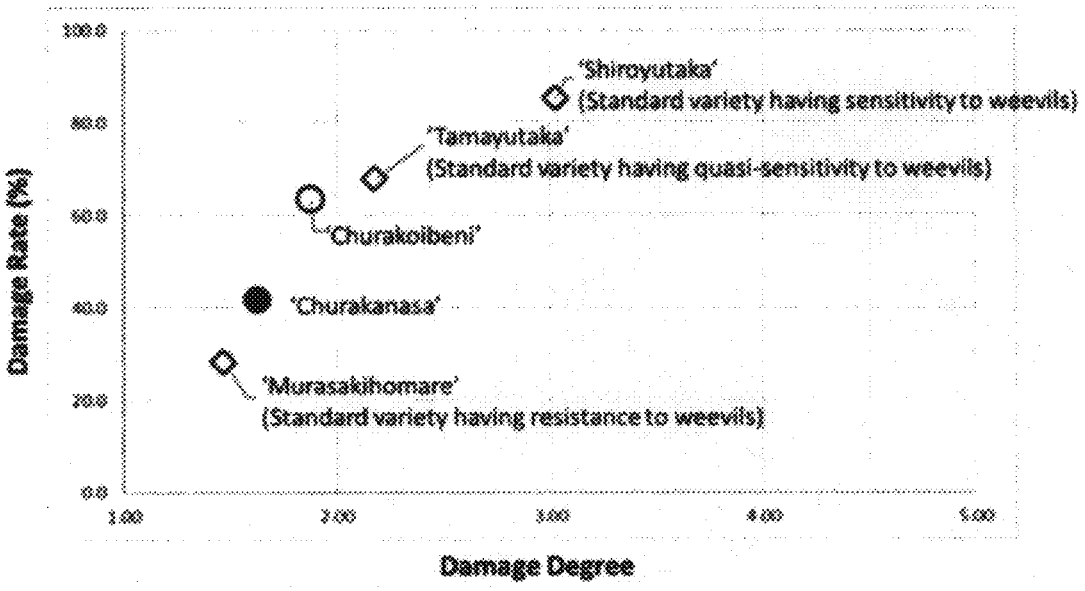
FIG. 8 is a graph showing weevil damage rate and damage degree for 'Churakanasa' as well as varieties 'Shiroyutaka', 'Tamayutaka', 'Churakoibeni', and 'Murasakihomare'.
Figure 9:
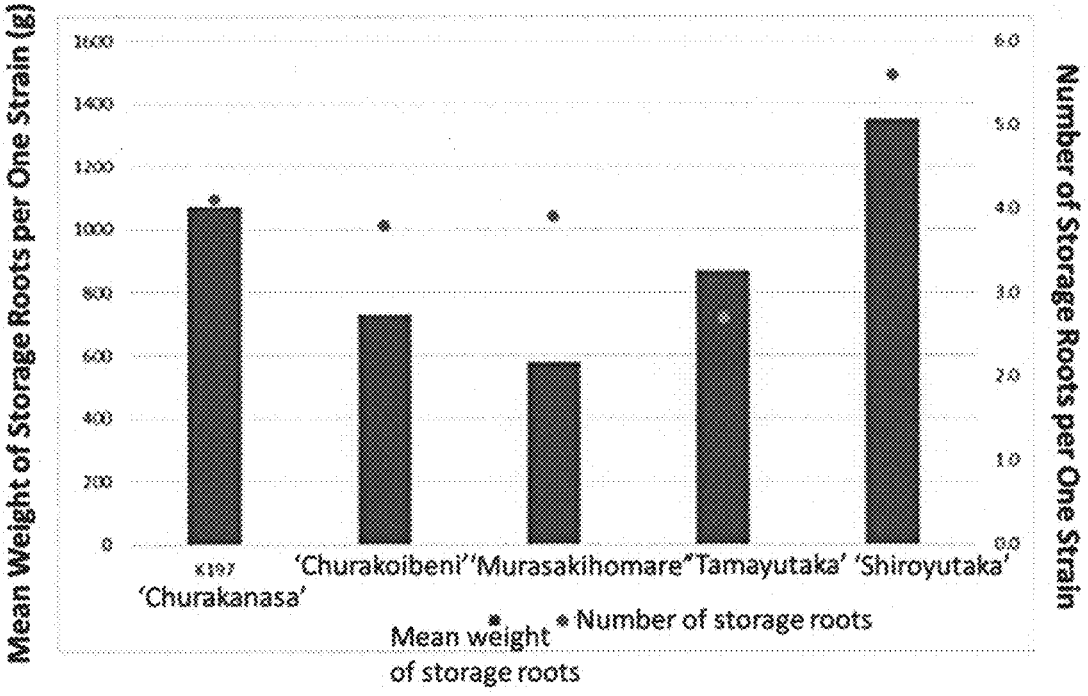
FIG. 9 is a graph showing storage root weight and number for 'Churakanasa' as well as varieties 'Churakoibeni', 'Murasakihomare', 'Tamayutaka', and 'Shiroyutaka'.

Species of the plant claimed: *Ipomoea batatas* (L.) Lam. The claimed plant is bred by hybridizing variety 'Purple Sweet Lord' (not patented) as the female parent and Indonesian native lineage '90IDN-47' (not patented) as the male parent.

Common names of the claimed plant's species include: sweet potato.

Characteristics of 'Churakanasa' provided herein were observed when the plant was cultivated at Yokoichi-machi, Miyazaki, Japan in open culture and at time points indicated in the Brief Description of the Drawings.

Sweet potato 'Churakanasa' is a lineage selected from a mating combination in which 'Purple sweet lord' having a purple color flesh and excellent appearance is used as a mother, and Indonesian native lineage, '90IDN-47' having soil rot resistance is used as a father.

Cross-breeding and collecting seeds were carried out at Kumamoto Region in 2009. Selection and breeding were carried out at Okinawa Region from 2011 onwards. To asexually reproduce 'Churakanasa', sprout cuttings were used as propagating materials and planted in Kumamoto. Based on the result of seedling individual selection test in Kumamoto in 2011, a lineage was selected which showed dark purple flesh color and was excellent in appearance and root tuberization, and was given the lineage number of 'Kyukei 09307-72'. Thereafter, 'Kyukei 09307-72' was used for the lineage selection preliminary test in Kumamoto in 2012, the lineage selection test in Kumamoto in 2013, the productivity check preliminary test in Okinawa in 2014, and the productivity check test in Okinawa in 2015. As a result, the yield of spring cultivation of the selected lineage in Okinawa is almost the same as that of 'Churakoibeni', and the selected lineage is excellent in resistance to soil rot, etc., and therefore, the system number of 'Kyukei 348' was assigned to the selected lineage in 2017. From 2017 onwards, in addition to spring cultivation, the yield was evaluated in the autumn cultivation in Okinawa, and the processability was evaluated by the actual users. From 2018 onwards, black rot disease (*Ceratocystis fimbriata*) resistance test in Nagasaki and soil rot resistance test in Tokushima have been carried out. As a result of examining various characteristics, the system name of 'Kyushu No. 197' was assigned to the finally selected lineage in December 2018. 'Kyushu No. 197' was named 'Churakanasa'. Incidentally, the field productivity test was carried out in Okinawa in 2016-2018.

Morphological Characteristics

The plant growth habit in a field is the spreading type. The length of primary shoots of the stem is similar to 'Ayamurasaki' (not patented) and 'Murasakimasari' (not patented) (131.8 cm). The length of internode of the stem is similar to 'Ayamurasaki' and 'Murasakimasari' (6.7 cm). The diameter of internode of the stem is larger than 'Ayamurasaki' and 'Murasakimasari' (7.06 mm). The anthocyanin coloration of the internode of stem is similar to 'Murasakimasari' and weaker than 'Ayamurasaki'. The anthocyanin coloration of tip of stem is weaker than 'Ayamurasaki' and stronger than 'Murasakimasari'. The anthocyanin coloration of node of stem is weaker than 'Ayamurasaki' and 'Murasakimasari'. The pubescence of tip is more dense than 'Ayamurasaki' and 'Murasakimasari'. The shape of the leaf blade is the single incision lobed type in Seed and Seedling Characteristics Classification Survey References (the old standard on March, 1981). The size of the leaf blade is larger than 'Ayamurasaki' and 'Murasakimasari' (215.2 $cm^2$); the number of lobes of the leaf blade is 3. The depth of lobing of the leaf blade is similar to 'Ayamurasaki' and deeper than 'Murasakimasari'. The color and the anthocyanin coloration on upper side of the leaf blade are green (139B) and weak, respectively. The extent of anthocyanin coloration on abaxial veins on lower side of the leaf blade is similar to 'Murasakimasari' and greater than 'Ayamurasaki'. The intensity of anthocyanin coloration on abaxial veins on lower side of the leaf blade is similar to 'Ayamurasaki' and 'Murasakimasari'. The anthocyanin coloration of nectary is stronger than 'Ayamurasaki' and 'Murasakimasari'. The main color on upper side and lower side of the young leaf blade are purplish brown (N82A) and green (139C), respectively. The anthocyanin coloration and length of the petiole is similar to 'Ayamurasaki' and 'Murasakimasari' (25.3 cm). The flowering in open-field culture is absent. Floral and fruit characteristics have not been observed to date. Sweet potato does not flower in the temperate zone.

The strength of the storage root's neck is medium. The position of the storage root (same as depth from the field surface to storage root) is medium, and the difficulty of digging (harvesting) the storage root (same as root tuber) is medium. The shape of storage root is elliptic, similar to 'Ayamurasaki' and 'Murasakimasari'. The uniformity in shape of storage roots is medium to low. The size of storage roots is less than 'Ayamurasaki' and 'Murasakimasari' (142 grams), and the uniformity in size of storage roots is medium to low. The colors of skin and flesh of the storage root are light purple (N79C) and purple (N79C), respectively. The depth of eyes of the storage root is similar to 'Murasakimasari' and more shallow than 'Ayamurasaki' as measured using visual observation. The skin roughness of the storage root is medium. The grooves, dehiscence and ridges of the storage root are all absent and the appearance is medium.

Ecological Characteristics

The timing (early or late) of sprouting from storage root is late. The uniformity in time of sprouting from different storage roots (almost simultaneous or not) is medium to high. The speed of sprout elongation is slow, and the number of sprouts is medium, as measured using visual observation, and the sprouting trait (same as sprouting habit) is poor and lower than that of 'Ayamurasaki' and 'Murasakimasari'.

Under the standard cultivation at the breeding place, the yield (total weight) of the good quality storage roots is lower than those of 'Ayamurasaki' and 'Murasakimasari'. The average yield for 'Churakanasa' is 183 kg/a, while the average yield for 'Murasakimasari' is 329 kg/a and average yield for 'Ayamurasaki' is 307 kg/a. Also, the percentage of dry matter content and the starch content are lower than those of 'Ayamurasaki' and 'Murasakimasari'.

The resistance to Southern root-knot nematode (*M. incognita*) is similar to 'Ayamurasaki' and less than 'Murasakimasari' and the resistance to Minami root-lesion nematodes (*P. coffeae*) is moderately strong. The resistance to black rot disease (*Ceratocystis fimbriata*) is medium. The resistance to soil rot is moderately strong, and the resistance to stem rot (*Fusarium oxysporum f*, sp. *batatas*) is medium. Storability of storage root is moderately difficult.

Quality Characteristics

The taste of steamed storage root is medium, and exceeds that of 'Ayamurasaki' and 'Murasakimasari'. The color value indicating the amount of anthocyanin content is a little higher than that of 'Churakoibeni', and lower than that of 'Ayamurasaki' and 'Murasakimasari'. The color of paste made from the flesh is a little more bluish than that of 'Ayamurasaki' and 'Murasakimasari'.

Varieties that are similar to 'Churakanasa' are 'Murasakimasari' and 'Ayamurasaki'. Characteristics of 'Murasakimasari' and 'Ayamurasaki' are compared in Tables 1 through 3 below. The Fifth Edition (2007) of "The Royal Horticulture Society Colour Chart" (R.H.S.) was used for color designations.

TABLE 1

Distinguishable characteristics between 'Churakanasa' and similar varieties

| Description of Characteristics | State of Expression in Candidate Variety 'Churakanasa' | State of Expression in Similar Variety ('Murasakimasari' or 'Ayamurasaki') |
|---|---|---|
| Young leaf blade: main color on upper side | purplish brown (N82A) | light green (140B) ('Murasakimasari') |
| Leaf blade: extent of anthocyanin coloration on abaxial veins on lower side | main vein | absent ('Ayamurasaki') |

TABLE 1-continued

Distinguishable characteristics between 'Churakanasa' and similar varieties

| Description of Characteristics | State of Expression in Candidate Variety 'Churakanasa' | State of Expression in Similar Variety ('Murasakimasari' or 'Ayamurasaki') |
|---|---|---|
| Leaf blade: intensity of anthocyanin coloration on abaxial veins on lower side | weak | very weak ('Ayamurasaki') |

TABLE 2

Description of physical characteristics of 'Churakanasa' and values for characteristics of similar varieties for year 2018

| Characteristics No. | Characteristics | Class values of candidate variety 'Churakanasa' | Class Values of most similar varieties 'Ayamurasaki' | 'Murasakimasari' |
|---|---|---|---|---|
| 1 | Plant: growth habit | spreading | spreading | spreading |
| 2 | Stem: length of primary shoots | short to medium (69.0 cm) | medium (99.9 cm) | medium (84.2 cm) |
| 3 | Stem: length of internode | medium (4.1 cm) | medium (4.9 cm) | medium (4.2 cm) |
| 4 | Stem: diameter of internode | medium (5.68 mm) | medium (5.33 mm) | medium (5.09 mm) |
| 5 | Stem: anthocyanin coloration of internode | medium | strong | medium |
| 6 | Stem: anthocyanin coloration of tip | medium | strong | weak |
| 7 | Stem: anthocyanin coloration of node and lateral branch | medium | strong | strong |
| 8 | Stem: pubescence of tip | dense | sparse | absent or very sparse |
| 9 | Leaf blade: size | small to medium (139.9 $cm^2$) | medium (148.1 $cm^2$) | small to medium (120.6 $cm^2$) |
| 10 | Leaf blade: number of lobes | three lobes | three lobes | three lobes |
| 12 | Only varieties with leaf blade lobes: Leaf blade: depth of lobing | moderate | moderate | shallow |
| 13 | Excluding ornamental variety: Leaf blade: color on upper side (excluding anthocyanin coloration) | green (139B) | green (141C) | green (135C) |
| 14 | Leaf blade: arrangement of the leaf | alternate | alternate | alternate |
| 15 | Leaf blade: length of the leaf | 12.5 cm | 12.7 cm | 11.4 cm |
| 16 | Leaf blade: width of the leaf | 11.2 cm | 11.6 cm | 10.5 cm |
| 17 | Leaf blade: margin | sinuate (not crenate) | sinuate (not crenate) | sinuate (not crenate) |
| 18 | Leaf blade: texture | smooth | smooth | smooth |

TABLE 2-continued

Description of physical characteristics of 'Churakanasa' and values for characteristics of similar varieties for year 2018

| Characteristics No. | Characteristics | Class values of candidate variety 'Churakanasa' | Class Values of most similar varieties 'Ayamurasaki' | 'Murasakimasari' |
|---|---|---|---|---|
| 19 | Excluding ornamental variety: Leaf blade: anthocyanin coloration on upper side | weak | weak | absent or very weak |
| 20 | Leaf blade: extent of anthocyanin coloration on abaxial veins on lower side | medium (main vein) | absent or very small | medium |
| 21 | Leaf blade: intensity of anthocyanin coloration on abaxial veins | weak | very weak | weak |
| 22 | Leaf blade: on lower side anthocyanin coloration of nectary | absent or very weak | absent or very weak | strong |
| 23 | Young leaf blade: main color on upper side | purplish brown (N82A) | purplish brown (77A) | light green (140B) |
| 24 | Young leaf blade: main color on lower side | Green (139C) | Green (139D) | Green (139D) |
| 25 | Petiole: anthocyanin coloration | weak | weak | weak |
| 26 | Petiole: length | medium (13.1 cm) | medium (12.5 cm) | medium (13.4 cm) |
| 29 | Storage root: shape | elliptic | elliptic | ovate |
| 30 | Storage root: ratio length/width | medium (2.5) | moderately elongated (4.7) | medium (2.7) |
| 31 | Storage root: number | medium (3.7) | medium (3.9) | medium (4.7) |
| 32 | Storage root: mean weight | small to medium (136 g) | medium (183 g) | small to medium (143 g) |
| 33 | Storage root: thickness of cortex relative to overall diameter | medium (0.050) | thick (0.070) | medium to thick (0.060) |
| 34 | Storage root: main color of skin | light purple (N79C) | medium purple (N79A) | medium purple (N79A) |
| 35 | Storage root: secondary color of skin | absent | absent | absent |
| 36 | Storage root: main color of flesh | purple (N79C) | purple (N79B) | purple (N79B) |
| 37 | Storage root: intensity of main color of flesh | medium | dark | dark |
| 38 | Storage root: secondary color of flesh | white (N155B) | absent | absent |
| 39 | Storage root: depth of eyes | medium | deep | shallow |
| 40 | Storage root: color of steamed flesh | purple (86A) | purple (N79C) | purple (N79C) |
| 44 | Southern root-knot nematode (*Meloisogyne*) resistance | medium | medium | moderately strong |

TABLE 2-continued

Description of physical characteristics of 'Churakanasa' and values for characteristics of similar varieties for year 2018

| Characteristics No. | Characteristics | Class values of candidate variety 'Churakanasa' | Class Values of most similar varieties 'Ayamurasaki' | 'Murasakimasari' |
|---|---|---|---|---|
| 45 | plant: temperature tolerance | 20° C.-35° C. | 20° C.-35° C. | 20° C.-35° C. |
| 46 | Productivity: the yield (total weight) of the good quality storage roots | 183 kg/a | 307 kg/a | 329 kg/a |
| 47 | Storability of storage root in storage house: the proportion of the number of rot individuals | 4/20 (30%) | 2/20 (10%) | 0/20 (0%) |

TABLE 3

Description of physical characteristics of 'Churakanasa' and values for characteristics of similar varieties for year 2019

| Characteristics No. | Characteristics | Class values of candidate variety 'Churakanasa' | Class Values of most similar varieties 'Ayamurasaki' | 'Murasakimasari' |
|---|---|---|---|---|
| 1 | Plant: growth habit | spreading | spreading | spreading |
| 2 | Stem: length of primary shoots | medium (131.8 cm) | medium (147.7 cm) | medium (147.0 cm) |
| 3 | Stem: length of internode | medium (6.7 cm) | medium (6 cm) | medium (7.3 cm) |
| 4 | Stem: diameter of internode | Medium to large (7.06 mm) | medium (5.87 mm) | medium (5.59 mm) |
| 5 | Stem: anthocyanin coloration of internode | medium | strong | medium |
| 6 | Stem: anthocyanin coloration of tip | medium | strong | weak |
| 7 | Stem: anthocyanin coloration of node and lateral branch | medium | strong | strong |
| 8 | Stem: pubescence of tip | dense | sparse | sparse |
| 9 | Leaf blade: size | medium to large (215.2 $cm^2$) | medium (190.0 $cm^2$) | medium (182.5 $cm^2$) |
| 10 | Leaf blade: number of lobes | three lobes | three lobes | three lobes |
| 12 | Only varieties with leaf blade lobes: Leaf blade: depth of lobing | moderate | moderate | shallow |
| 13 | Excluding ornamental variety: Leaf blade: color on upper side (excluding anthocyanin coloration) | green (139B) | green (141C) | green (135C) |
| 14 | Leaf blade: arrangement of the leaf | alternate | alternate | alternate |

TABLE 3-continued

Description of physical characteristics of 'Churakanasa' and values for characteristics of similar varieties for year 2019

| Characteristics No. | Characteristics | Class values of candidate variety 'Churakanasa' | Class Values of most similar varieties 'Ayamurasaki' | 'Murasakimasari' |
|---|---|---|---|---|
| 15 | Leaf blade: length of the leaf | 15.4 cm | 14.4 cm | 14.0 cm |
| 16 | Leaf blade: width of the leaf | 14.0 cm | 13.1 cm | 13.0 cm |
| 17 | Leaf blade: margin | sinuate (not crenate) | sinuate (not crenate) | sinuate (not crenate) |
| 18 | Leaf blade: texture | smooth | smooth | smooth |
| 19 | Excluding ornamental variety: Leaf blade: anthocyanin coloration on upper side | weak | weak | absent or very weak |
| 20 | Leaf blade: extent of anthocyanin coloration on abaxial veins on lower side | medium (main vein) | absent or very small | medium |
| 21 | Leaf blade: intensity of anthocyanin coloration on abaxial veins on lower side | weak | very weak | weak |
| 22 | Leaf blade: anthocyanin coloration of nectary | strong | absent or very weak | absent or very weak |
| 23 | Young leaf blade: main color on upper side | purplish brown (N82A) | purplish brown (77A) | light green (140B) |
| 24 | Young leaf blade: main color on lower side | green (139C) | green (139D) | green (139D) |
| 25 | Petiole: anthocyanin coloration | weak | weak | weak |
| 26 | Petiole: length | medium (25.3 cm) | medium (24.3 cm) | medium (25.7 cm) |
| 29 | Storage root: shape | elliptic | elliptic | ovate |
| 30 | Storage root: ratio length/width | medium to moderately elongated (3.4) | moderately elongated (4.9) | medium to moderately elongated (3.5) |
| 31 | Storage root: number | medium (3.3) | medium to many (5.0) | medium to many (5.9) |
| 32 | Storage root: mean weight | medium (142 g) | medium to large (205 g) | medium (160 g) |
| 33 | Storage root: thickness of cortex relative to overall diameter | medium (0.057) | thick (0.072) | medium to thick (0.064) |
| 34 | Storage root: main color of skin | light purple (N79C) | medium purple (N79A) | medium purple (N79A) |
| 35 | Storage root: secondary color of skin | absent | absent | absent |
| 36 | Storage root: main color of flesh | purple (N79C) | purple (N79B) | purple (N79B) |
| 37 | Storage root: intensity of main color of flesh | medium | dark | dark |
| 38 | Storage root: secondary color of flesh | white (N155B) | absent | absent |
| 39 | Storage root: depth of eyes | shallow | deep | shallow |
| 40 | Storage root: color of steamed flesh | purple (86A) | purple (N79C) | purple (N79C) |
| 44 | Southern root-knot nematode (*Meloisogyne*) resistance | medium | medium | moderately strong |
| 45 | plant: temperature tolerance | 20° C.-35° C. | 20° C.-35° C. | 20° C.-35° C. |
| 46 | Productivity: the yield (total weight) of the good quality storage roots | 183 kg/a | 307 kg/a | 329 kg/a |
| 47 | Storability of storage root in storage house: the proportion of the number of rot individuals | 11/20 (55%) | 2/20 (10%) | 4/20 (20%) |

The sprouting trait (same as sprouting habit) of 'Churakanasa' is poor and lower than that of 'Ayamurasaki' and 'Murasakimasari'. The extent and the intensity of anthocyanin coloration on abaxial veins on lower side of the leaf blade of 'Churakanasa' are the same as that of 'Murasakimasari' and are larger and stronger than those of 'Ayamurasaki'. The color on upper side of young leaf of 'Churakanasa' is purplish brown (N82A), which is the same as 'Ayamurasaki' and different from 'Murasakimasari'. The strength of the storage root's neck of 'Churakanasa' is medium. The shape of storage root of 'Churakanasa' is elliptic and spindle. The skin color of storage root of 'Churakanasa' is light purple (N79C) ,which is lighter than that of 'Ayamurasaki'. The appearance of 'Churakanasa' is medium. There is no groove, ridge and dehiscence on the storage root of 'Churakanasa'.

Compared to 'Ayamurasaki' and 'Murasakimasari', in standard cultivation, the mean weight of the good quality potatoes (storage roots) and the total weight of the good quality storage roots of 'Churakanasa' are lower. The mean weight of storage roots of 'Churakanasa' is 183 kg/a, while the mean weight of storage roots is 329 kg/a for 'Murasakimasari' and 307 kg/a for 'Ayamurasaki'. Also under earlier harvest condition, the mean weight of the good quality storage roots and the number of good quality storage roots per one plant of 'Churakanasa' are low, and the total weight of the good quality storage roots of 'Churakanasa' is lower than that of 'Ayamurasaki'. The number of good quality storage roots per one plant of 'Churakanasa' is low, and the mean weight of the good quality storage roots of 'Churakanasa' is a little light, too. Therefore the total weight of the good quality storage roots of 'Churakanasa' is lower than that of 'Purple Sweet Lord'.

The steamed flesh color of 'Churakanasa' is purple (86A) quality of flesh in standard cultivation is a little crumbly and the taste of flesh is medium, which exceeds that of 'Ayamurasaki' and 'Murasakimasari'. The color value of anthocyanin of 'Churakanasa' is a little higher than that of 'Churakoibeni', in the breeding place. The color value of anthocyanin of 'Churakanasa' is lower than that of 'Ayamurasaki'. In the breeding place, the color of paste of 'Churakanasa' is a little more bluish than that of 'Churakoibeni' (the value b* of 'Churakanasa' is a little smaller). The variable b* is commonly used to represent color difference. The higher the value of b*, the more yellowish the represented color, and the lower the value of b*, the more bluish the represented color.

The paste made from the flesh of 'Churakanasa' is different from 'Churakoibeni' in color tone and the paste is moderately harder than that of 'Churakoibeni', but there is no particular problem associated with this hardness. It is easy to peel and process. In addition, the flavor of 'Churakanasa' is better than 'Churakoibeni', and it is suitable for processed products. After preparation of the paste, Beniimo tarts were prepared with use of secondary material according to a standard recipe, and sensory evaluation was conducted. The difference in the color tone of 'Churakanasa' and 'Churakoibeni' is such that it can only be understood by comparing them side by side, and there is no problem. The paste of 'Churakanasa' tends to become lumpy during processing, but that is no problem. Compared to 'Churakoibeni', it has better sweet potato flavor and taste.

Tests for storability of storage root in storage house and laboratory were also carried out. Just after harvest, storage root were stored in storage house (about 18° C.) and laboratory (non-controlled temperature). Judgement of storability of storage root in storage house was based on the proportion of the number of rot individuals in late February: 0.0% is considered easy; 0.1% to 10.0% is considered moderately easy; 10.1% to 25.0% is considered medium; 25.1% to 40.0% is considered moderately difficult, 40.1% and higher is considered difficult. Judgement of storability of storage root in laboratory was based on the proportion of the number of rot individuals in late February: 0.0% to 15.0% is considered easy; 15.1% to 35.0% is considered moderately easy; 35.1% to 55.0% is considered medium; 55.1% to 75.0% is considered moderately difficult, 75.1% and higher is considered difficult. Storability of storage root of 'Churakanasa' in storage house and laboratory is moderately difficult and worse than that of 'Ayamurasaki'. Tests for Southern root-knot nematode (*M. incognita*) resistance and Minami root-lesion nematodes (*P. coffeae*) were carried out. The resistance evaluation on a scale of weak, moderately weak, medium, moderately strong, and strong was carried out using visual observation, on the basis of symptoms on the roots of sweet potatoes which were cultivated on a field subsequent to cropping of sensitive sweet potatoes on the field in a preceding year. Southern root-knot nematode (*M. incognita*) resistance of 'Churakanasa' is medium and the resistance to Minami root-lesion nematodes (*P. coffeae*) is moderately strong. In characterization tests, the soil rot resistance of 'Churakanasa' was judged to be moderately strong. For the soil rot resistance test, the test site was naturally infested fields in Okinawa. Fertilization condition was $N:P_2O_5:K_2O=0.45:0.45:0.90$ (kg/a). Cultivation conditions were mulching-free cultivation, 80 cm ridges interval×30 cm strains interval, 5 strains/block×3 repeats. Planting was done on Apr. 28, 2014 with excavation on Sep. 29, 2014. Additional planting was done on May 18, 2015 with excavation on Oct. 9, 2015. Additional planting was also done on Jun. 8, 2016 with excavation on Nov. 18, 2016. Damage investigation involved dividing into stems and storage roots at harvesting, counting the blotches respectively, and then converting them into an evaluation value. The attitude evaluation on a scale of one to six was carried out. The stem or storage root having no blotch is evaluation value 1, having 1 to 3 blotches is evaluation value 2, having 4 to 6 blotches is evaluation value 3, having 7 to 9 blotches is evaluation value 4, having 10 or more blotches is evaluation value 5 and blighted strain is evaluated at 6. Judgement criteria based on this was that an evaluation value less than 2 is strong, 2 to less than 3 is moderately strong, 3 to less than 4 is moderately weak, and evaluation value of 4 or more than 4 is "weak". The soil rot resistance of 'Churakanasa' was found to be moderately strong. In the characterization tests, the resistance of 'Churakanasa' to black rot disease was judged to be medium. In other tests, the resistance of 'Churakanasa' to Southern root-knot nematode (*M. incognita*) is moderately weak, the soil rot resistance of 'Churakanasa' is medium, and the resistance of 'Churakanasa' to stem rot (*Fusarium oxysporum f*, sp. *batatas*) is medium.

Tests for resistance to weevils were also carried out. The test site was a field in Okinawa. Fertilization conditions were $N:P_2O_5:K_2O=0.45:0.45:0.90$ (kg/a). Cultivation conditions were mulching-free cultivation, 80 cm ridges interval×30 cm strains interval, 10 strains/block×3 repeats. Planting was done on May 13, 2016 with excavation on Oct. 25, 2016. Additional planting was done on May 19, 2017 with excavation on Nov. 10, 2017. Additional planting was also done on May 11, 2018 with excavation on Oct. 29, 2018. About 2-3 months after planting, 40 piglets (*Euscepes postfasciatus*) were left per block to investigate the harvested material. *Cylas formicarius* were left to spontaneous invasion. 'Churakanasa' is determined to be damaged if there is at least one insect damage mark on the tuber (storage root) cross section sliced to 3 mm thickness. A sound plant without insect damage mark on the tuber cross section sliced to 3 mm thickness is called stage 1, if insect damage mark is less than 5% of the cross section the stage is 2, if insect damage mark is 5% or more to less than 30% of the cross section the stage is 3, if insect damage mark is 30% or more to less than 50% of the cross section the stage is 4, and if insect damage mark is 50% or more of the cross section the stage is 5, the attitude evaluation of the five stages was carried out. Judgement was based on damage rate: 10 is considered strong; 11 to 30 is considered slightly strong; 31 to 50 is considered medium; 51 to 70 is considered slightly weak, 71 and higher is considered weak. The damage degree and the damage rate of 'Churakanasa' to the weevils tend to be lower than those of existing varieties in the same field, and the total yield of 'Churakanasa' including the damaged storage roots shows a high level even in the presence of the weevils.

'Churakanasa' is not suitable for cultivation in Kyushu because the yield (total weight) of the good quality storage roots is small and the sprouting quality is poor at the cultivation site (Miyakonojo City, Miyazaki Prefecture).

It will be understood that the average size of the plant and fruit may vary with location, season, nutrition, irrigation, etc.

What is claimed is:

1. A new and distinct *Ipomoea batatas* plant named 'Churakanasa' as illustrated and described.

* * * * *